Aug. 9, 1949. T. J. MORRIS Plant Pat. 860
ROSE PLANT
Filed Sept. 29, 1947
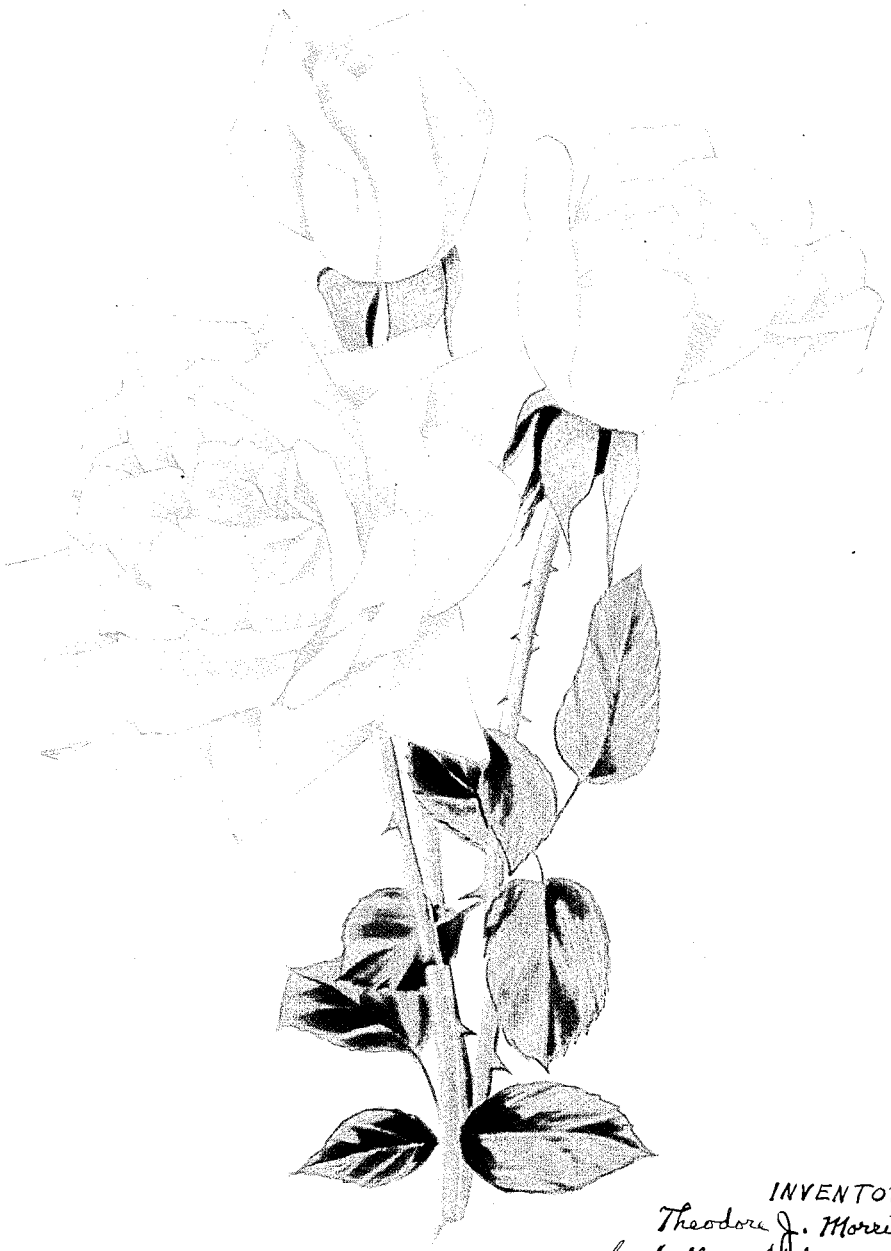
INVENTOR
Theodore J. Morris, Dec'd
by Lillian Adele Morris
Administratrix
By Orville M Kile
Plant Pat. Agt.

Patented Aug. 9, 1949

Plant Pat. 860

UNITED STATES PATENT OFFICE

860

ROSE PLANT

Theodore J. Morris, deceased, late of Van Nuys, Calif., by Lillian Adele Morris, administratrix, Van Nuys, Calif., assignor to Germain Seed and Plant Company, Los Angeles, Calif.

Application September 29, 1947, Serial No. 776,778

1 Claim. (Cl. 47—61)

This new variety is particularly vigorous in growth and prolific in the production of flowers. Its flower is large and of a vivid color. It has a moderate fragrance and keeps as a cut flower a great deal longer than the average of similar flowers.

This variety resulted from a cross between the variety Poinsettia and an unnamed seedling, the cross having been made in the Germain greenhouses at Van Nuys, California. It has been asexually reproduced through several generations and its characteristics appear to be firmly fixed.

The accompanying illustrations show in full and approximately accurate color, three specimens of the flowers of this new variety in various stages of opening, together with portions of the stems and foliage.

In the following detailed description of the plant and flower, color plate references indicate the Horticultural Colour Chart issued by the British Colour Council. Where no chart reference is given, the ordinary dictionary term is intended.

*The plant*

Growth: Very vigorous upright bush.
Propagation: Easy.
Blooming habit: Continuous and profuse.
Disease resistance: Very resistant to mildew and black spot.
Foliage:
- *Leaflets.*—Five.
- *Size.*—Large.
- *Quantity.*—Abundant.
- *Color.*—Dark green on upper surface, light green on under surface.
- *Shape.*—Oval pointed. Edges singly and sharply serrated.
- *Texture.*—Leathery and smooth.
- *Leaf stem or rachis.*—Reddish green with some prickles on under side.
- *Stipules.*—Medium size. Smooth point of tips curved outward.

Wood:
- *Old wood.*—Smooth. Dark green and greenish bronze in colour.
- *New wood.*—Smooth. Light green.
- *Stems.*—Long, stiff, and strong.
- *Thorns.*—Many. Long, broad-based and downward-hooked. Usually bronzy green.

*The flower*

Bud:
- *Size.*—Large.
- *Form.*—Very long pointed.

- *Opening.*—Opens slowly. Not affected by adverse conditions.
- *Color.*—At first Azalea Pink (Plate 618/1). Later, Crimson (Plate 22/1 and 22/2), with reverse of petals Azalea Pink.
- *Calyx and sepals.*—Long, smooth, simple, with smooth edges. Reflex early. Has Briar odor when rubbed.
- *Peduncle.*—Long, stiff, and strong. Light green on small canes, bronzy on heavy canes.

Bloom:
- *Size.*—Large; approximately 5½ inches across when fully expanded.
- *Borne.*—Singly.
- *Petalage.*—Very double, with about 45 petals.
- *Form.*—High-centered, with outer petals reflexing and quilling like a cactus dahlia. This form is retained to the end.
- *Color.*—General color effect is Crimson (Plate 22). Upper surface of central petals is Carmine (Plate 21/1) with a large aiglet of Indian Yellow (Plate 6/2) at the base. Outer petals are slightly lighter. Reverse of petals, approximately Azalea Pink (Plate 618/1). The color lightens as it ages and on the third day is approximately Crimson (Plate 22/2).
- *Lasting quality.*—Very long lasting, both on bush and as cut flower.

Petals:
- *Texture.*—Thick and soft.
- *Aspect.*—Inside satiny; outside silky and shiny.
- *Shape.*—Approximately round with point at top.
- *Arrangement.*—Center irregular and loose.
- *Fragrance.*—Moderate tea scent.
- *Persistence.*—Petals drop off cleanly.

Reproductive organs:
- *Stamens.*—Golden yellow with salmon filaments. Medium in size. Arrangement regular around pistils.
- *Pistils.*—Bunched. Medium size and even length. Yellow.
- *Ovaries.*—Some protruding from calyx.
- *Fruit.*—Variety is fertile with its own pollen. Round headed, smooth, yellow, recurved, and early falling.

*Comparison*

The known variety most like this new variety is Los Angeles, the principal differences between the two varieties being as follows:

1. The new variety has considerably more vigor of growth and strength of stem.

2. The new variety is more prolific in the production of flowers.

3. The flowers of the two varieties fall in different color ranges.

4. Flowers of the new variety have greater petalage and more fragrance.

5. Flowers of the new variety last much longer as cut flowers.

6. The new variety has a more pointed bud.

7. The petals of the new variety are more quilled.

Having thus disclosed this invention, I claim for the inventor:

The new and distinct variety of hybrid tea rose plant, substantially as herein disclosed, characterized particularly by its vigor of growth; its strength of stem; its prolific blooming habit; its long-pointed bud; and its flower combining good keeping qualities, large petalage, tea fragrance, Azalea Pink to Crimson colour, and irregularly arranged quilled petals.

LILLIAN ADELE MORRIS,
*Administratrix of the Estate of Theodore J. Morris, Deceased.*

No references cited.